(12) United States Patent
Perez

(10) Patent No.: US 6,544,286 B1
(45) Date of Patent: Apr. 8, 2003

(54) PRE-FABRICATED CORNEAL TISSUE LENS METHOD OF CORNEAL OVERLAY TO CORRECT VISION

(75) Inventor: Edward Perez, Menlo Park, CA (US)

(73) Assignee: Tissue Engineering Refraction, Inc., Menlo Park, CA (US)

( * ) Notice: Subject to any disclaimer, the term of this patent is extended or adjusted under 35 U.S.C. 154(b) by 0 days.

(21) Appl. No.: 09/618,580

(22) Filed: Jul. 18, 2000

(51) Int. Cl.[7] .................................................. A61F 2/14
(52) U.S. Cl. ........................................ 623/5.16; 623/4.1
(58) Field of Search .............................. 623/5.16, 5.11, 623/4.1

(56) References Cited

U.S. PATENT DOCUMENTS

| | | |
|---|---|---|
| 4,346,482 A | 8/1982 | Tennant et al. |
| 4,646,720 A | 3/1987 | Peyman et al. |
| 4,662,881 A | 5/1987 | Nordan |
| 4,676,790 A | 6/1987 | Kern |
| 4,715,858 A | 12/1987 | Lindstrom |
| 4,793,344 A | 12/1988 | Cumming et al. |
| 5,171,318 A | 12/1992 | Gibson et al. |
| 5,192,316 A | 3/1993 | Ting |
| 5,213,720 A | 5/1993 | Civerchia |
| 5,374,515 A | 12/1994 | Parenteau et al. |
| 5,522,888 A | 6/1996 | Civerchia |
| 5,716,633 A | 2/1998 | Civerchia |
| 5,827,641 A | 10/1998 | Parenteau et al. |
| 5,919,185 A | 7/1999 | Peyman |
| 6,036,683 A | 3/2000 | Jean et al. |
| 6,187,053 B1 | 2/2001 | Minuth |
| 6,280,435 B1 | 8/2001 | Odrich et al. |
| 6,280,469 B1 | 8/2001 | Terry et al. |

OTHER PUBLICATIONS

Chen, K–H. et al. (Oct. 2001). "Transplantation of adult human corneal endothelium ex vivo: a morphologic study," *Cornea* 20(7):731–737.

Joo, C–K et al. (Feb. 2000). "Repopulation of denuded murine Descemet's membrane with life–extended murine corneal endothelial cells as a model for corneal cell transplantation," *Graefes Archive for Clinical and Experimental Ophathalmology* 238(2):174–180.

Schwab, Ivan R. and Isseroff, R. Rivkah, (2000). "Bioengineered corneas—the promise and the challenge" *New England Journal of Medicine* 343(2):136–138.

Tsai, Ray Jui–Fang et al., (2000). "Reconstruction of damaged corneas by transplantation of autologous limbal epithelial cells" *New England Journal of Medicine* 343(2):86–93.

Primary Examiner—Corrine McDermott
Assistant Examiner—Thomas Barrett
(74) Attorney, Agent, or Firm—Morrison & Foerster LLP

(57) ABSTRACT

This invention relates to a contact lens made of donor corneal tissue, to a method of preparing that lens, and to a technique of placing the lens on the eye. The lens is made of donor corneal tissue that is acellularized by removing native epithelium and keratocytes. These cells are replaced with human epithelium and keratocytes to form a lens that has a structural anatomy similar to human cornea. The ocular lens is used to correct conditions such as astigmatism, myopia, aphakia, and presbyopia.

86 Claims, 4 Drawing Sheets

PRE-FABRICATED CORNEAL TISSUE LENS METHOD OF CORNEAL OVERLAY TO CORRECT VISION

FIELD OF THE INVENTION

This invention is in the field of ophthalmology. More particularly, it relates to a living contact lens made of donor corneal tissue, to a method of preparing that lens, and to a technique of placing the lens on the eye.

BACKGROUND OF THE INVENTION

The visual system allows the eye to focus light rays into meaningful images. The most common problem an ophthalmologist or optometrist will encounter is that of spherical ammetropia, or the formation of an image by the eye which is out of focus with accommodation due to an improperly shaped globe. The ophthalmologist or optometrist determines the refractive status of the eye and corrects the optical error with contact lenses or glasses.

Many procedures have been developed to correct spherical ammetropia by modifying the shape of the cornea. Light entering the eye is first focused by the cornea, which possesses approximately 75% of the eye's overall refractive power. The majority of refractive operations involve either decreasing or increasing the anterior curvature of the cornea.

The procedures in early corneal refractive surgery such as keratophakia and keratomileusis were originally developed to correct myopia and involved removing a corneal disc from the patient with a microkeratome. The removed corneal disc was then frozen prior to reshaping the posterior surface with a cryolathe. After thawing, the disc was returned to the eye and secured with sutures.

Epikeratophakia, as described in U.S. Pat. No 4,662,881, is a procedure that involves inserting a precut donor corneal tissue lens with bevelled edges into corresponding grooves in recipient cornea. The lens is then sutured to the corneal bed. The donor lens is lyophilized and requires rehydration before placement on recipient cornea.

These techniques and their variations were generally considered to be unsuccessful due to frequent complications involving irregular astigmatism, delayed surgical healing, corneal scarring, and instability of the refractive result. The problems were attributed to the technical complexity of the procedures as well as to the distortion in architecture of the corneal tissue secondary to lens manipulation. For example, in epikeratophakia, epithelial irregularity is induced by lyophilization of the donor lens. Freezing of the lenticule in keratophakia and keratomileusis also causes severe damage to epithelial and stromal cells and disrupts the lamellar architecture of the cornea.

The present invention is a pre-fabricated lens made of donor corneal tissue obtained from tissue sources such as human or animal cornea. The lens is a corneal disc that is preferably shaped on the posterior surface generally to conform in shape to the eye's anterior surface. The inventive lens may be shaped by an ablative laser, e.g., by an excimer laser or other suitable laser. The corneal lenticule is living tissue that has not been frozen, lyophilized, or chemically modified, e.g., fixed with glutaraldehyde to crosslink corneal tissue. Pre-existing keratocytes are removed and then replaced with human keratocytes to decrease antigenicity. After removal of epithelium in the central zone of the recipient's cornea, the lens is placed on this zone in the same manner that a contact lens is placed on the eye.

Ocular lenses found in the prior art do not use native cornea, but are formulated using soluble collagen such as collagen hydrogels, e.g., polyhydroxyethylmethacrylate, or other biocompatible materials. For example, in U.S. Pat. No. 5,213,720, to Civerchia, soluble collagen is gelled and crosslinked to produce an artificial lens. In addition to hydrogels, U.S. Pat. No. 4,715,858, to Lindstrom, discloses lenses made from various polymers, silicone, and cellulose acetate butyrate.

In the cases where ocular lenses use corneal tissue, the lenses are either corneal implants or require a separate agent to adhere the lens to the corneal bed. U.S. Pat. No. 5,171,318, to Gibson et al., and U.S. Pat. No. 5,919,185, to Peyman, relate to a disc of corneal tissue that is partially or entirely embedded in stroma. The ocular lens device disclosed in U.S. Pat. No. 4,646,720, to Peyman et al., and U.S. Pat. No. 5,192,316, to Ting, is attached to recipient cornea with sutures. The corneal inlay described in U.S. Pat. No. 4,676,790, to Kern, is bonded to recipient cornea using sutures, laser welding, or application of a liquid adhesive or crosslinking solution.

The ocular lens device of this invention does not alter the anatomical structure of corneal tissue. U.S. Pat. No. 4,346,482, to Tennant et al., discloses a "living contact lens" consisting of donor cornea that has been anteriorly curved for correction of vision. However, this lens is frozen prior to reshaping on a lathe which results in stromal keratocyte death. U.S. Pat. No. 4,793,344, to Cumming et al., also describes a donor corneal tissue lens that is modified by treatment with a gluteraldehyde fixative that preserves the tissue and prevents lens swelling. This treatment alters the basic structure of the corneal lenticule by crosslinking the tissue.

Furthermore, the cited documents do not show any methods of lens preparation that remove native corneal tissue cells and replace them with cells cultivated from human cornea. My inventive device is devitalized of native epithelium and keratocytes to create an acellular corneal tissue, and then revitalized with human epithelium and keratocytes. An attempt to construct a so-called "corneal tissue equivalent" was shown in U.S. Pat. No. 5,374,515, to Parenteau et al. However, the collagen used in that "equivalent" is obtained from bovine tendon instead of from cornea. The added keratocytes and epithelium are also not from human sources. The tissue using these cell culturing procedures is also quite fragile.

An excimer laser is used to reform a cornea via the "laser in situ keratomileusis" (LASIK) procedure. In this technique, an excimer laser is used to perform stromal photoablation of a corneal flap or in situ photoablation of the exposed stromal bed. Studies have shown that the inaccuracy of correction by this procedure may be as much as one diopter from the desired value. Lenses (contacts and spectacles), in contrast, are able to correct within 0.25 diopters of the desired value.

U.S. Pat. No. 6,036,683, to Jean et al., shows the use of a laser to reshape the cornea. However, the laser changes the native structure of the cornea by irreversibly coagulating collagen. Post-laser relaxation of collagen is not possible with this treatment.

This invention is a pre-fabricated donor contact lens that adheres to recipient cornea without sutures. The lens preserves the anatomy of normal corneal tissue. The donor lens can be obtained from human and animal sources, is devitalized of native keratocytes and epithelium to create an acellular tissue, and then revitalized with human keratocytes and epithelium to maintain lens viability and decrease antigenicity. The inventive corneal overlay technique may be completed under local anesthesia as well as general anesthesia, and the availability of a precut lens will greatly decrease procedure time, patient cost, and risk of operative complications. The duration of healing will also be reduced due to the implementation of a lens already repopulated with keratocytes.

SUMMARY OF THE INVENTION

This invention is a pre-fabricated ocular contact lens device having a lens core made of donor corneal tissue from tissue sources such as human or animal cornea. The device has a generally convex anterior surface and a concave posterior surface. The stroma portion of the lens core may be repopulated with replaced keratocytes and the anterior surface is preferably covered with a replaced epithelium. The lens core adheres to recipient cornea without sutures.

The lens core may be variously used to correct astigmatism, myopia, aphakia, and presbyopia. The lens core may be made of transgenic or xenogenic corneal tissue and have a clarity at least 85% of that of human corneal tissue of a corresponding thickness. The lens core is not frozen, lyophilized, or chemically treated with a fixative. However, variations of the device may contain therapeutic agents, growth factors, or immunosuppressive agents.

Another component of the invention is a method for preparing the lens device. After sharp dissection of a lenticule from donor corneal tissue, the posterior surface is shaped using an ablative laser, such as an excimer laser or other suitable shaping lasers. Native epithelium and keratocytes are removed and then replaced with human epithelium and keratocytes.

Another portion of the invention is a method of corneal overlay that involves de-epithelialization of a portion of the anterior surface of the recipient cornea and placement of the inventive ocular lens device upon that anterior surface.

DETAILED DESCRIPTION

Figure 1:
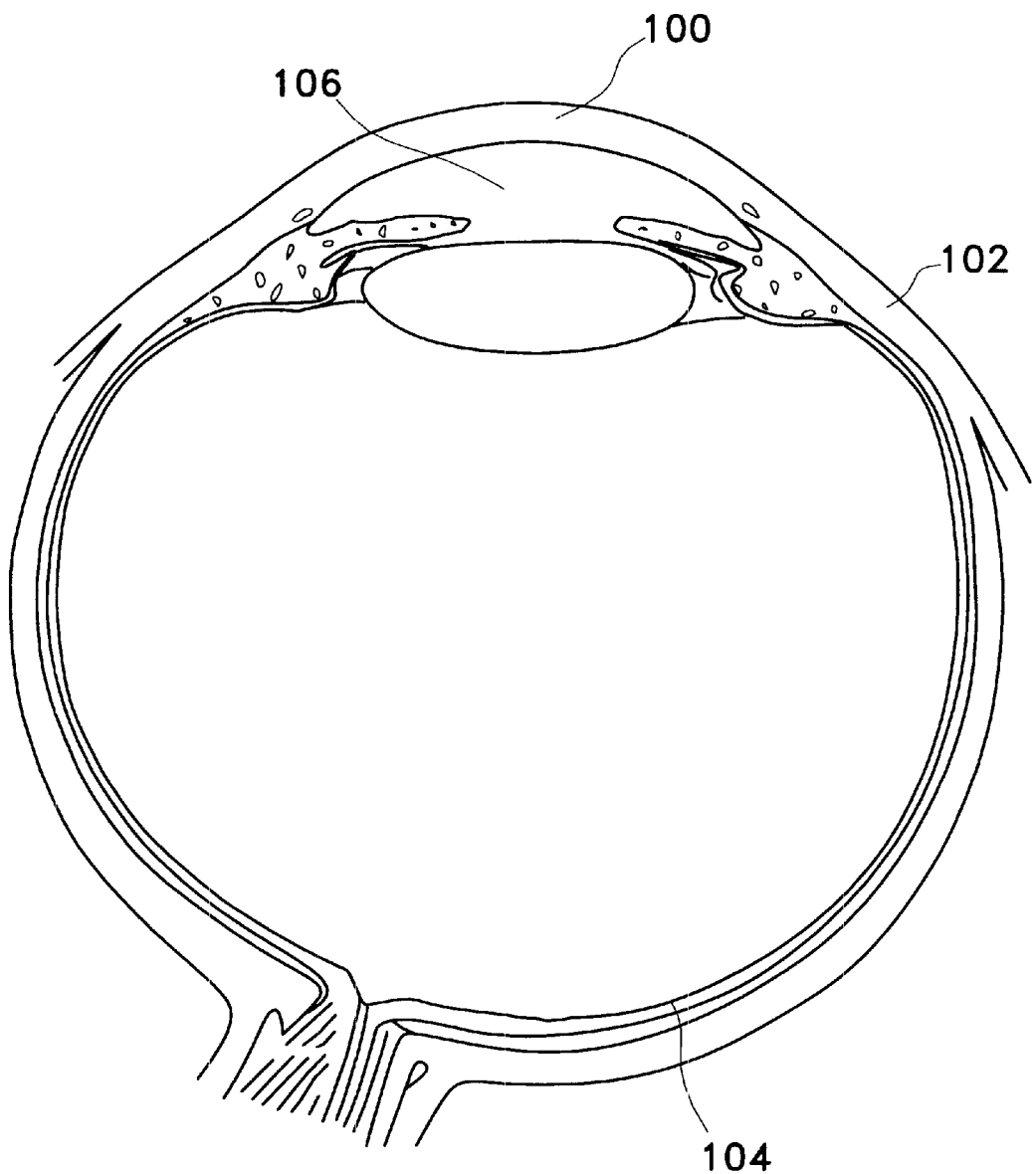
FIG. 1 is a superior, cross-sectional view of the eye.

The eye is designed to focus light onto specialized receptors in the retina that turn quanta of light energy into nerve action potentials. As shown in FIG. 1, light rays are first transmitted through the cornea (100) of the eye. The cornea is transparent due to the highly organized structure of its collagen fibrils. The margins of the cornea merge with a tough fibrocollagenous sclera (102) and is referred to as the corneo-scleral layer.

The cornea (100) is the portion of the corneo-scleral layer enclosing the anterior one-sixth of the eye. The smooth curvature of the cornea is the major focusing power of images on the retina (104) and it provides much of the eye's 60 diopters of converging power. The cornea is an avascular structure and is sustained by diffusion of nutrients and oxygen from the aqueous humor (106). Some oxygen is also derived from the external environment. The avascular nature of the cornea decreases the immunogenicity of the tissue, increasing the success rate of corneal transplants.

The cornea consists of five layers. The outer surface is lined by stratified squamous epithelium which is about 5 cells thick. Failure of epithelialization results in necrosis of the stromal cap and potential scarring of recipient cornea. The epithelium is supported by a specialized basement membrane known as Bowman's membrane, which gives the cornea a smooth optical surface. The bulk of the cornea, the substantia propria (stroma), consists of a highly regular form of dense collagenous connective tissue forming thin lamellae. Between the lamellae are spindle-shaped keratocytes which can be stimulated to synthesize components of the connective tissue. The inner surface of the cornea is lined by a layer of flattened endothelial cells which are supported by Descemet's membrane, a very thick elastic basement membrane.

Figure 2A:
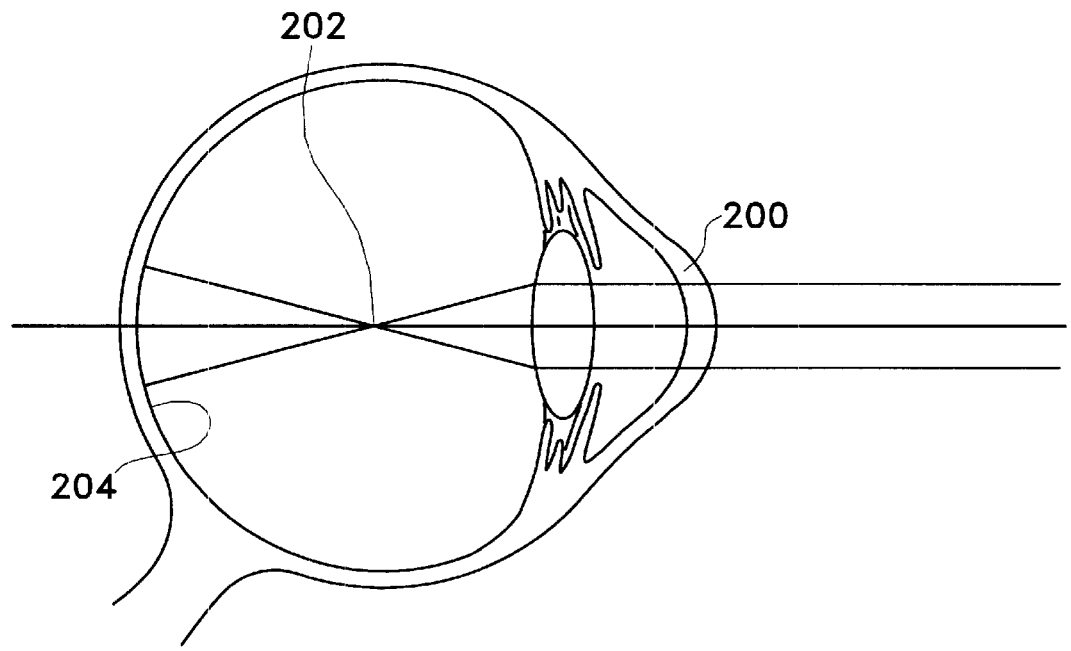
FIG. 2A is a side view of the focusing point in myopia.
Figure 2B:
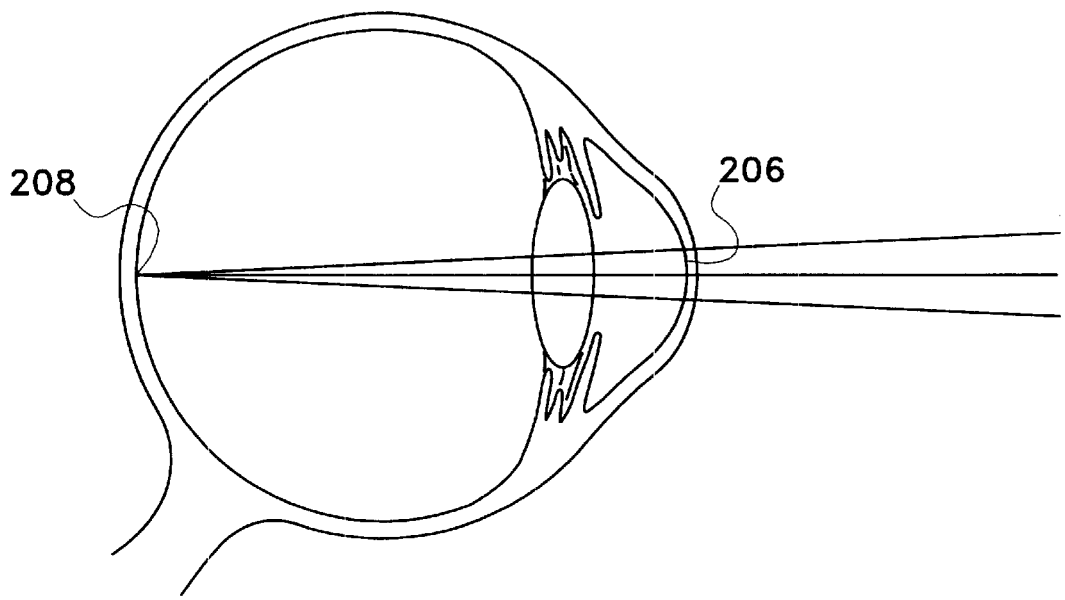
FIG. 2B is a side view of a focusing point corrected by flattening the anterior curvature of the cornea.

As previously mentioned, the focusing power of the cornea is primarily dependent on the radius of curvature of its external surface. In myopia, as seen in FIG. 2A, increased curvature of the cornea (200) causes the focusing point of light rays (202) to fall short of the retina (204). In FIG. 2B, flattening the anterior curvature of the cornea (206) corrects the focal point (208).

Inventive Lens Structure

The inventive contact lens is of a size and configuration that upon installation on the cornea, supplements the curvature of the cornea to correct conditions such as astigmatism, myopia, hyperopia, presbyopia, and aphakia. The lens core may comprise or consist essentially of acellular donor corneal tissue which has been re-vitalized and then placed on a de-epithelialized host cornea; the lens core is formed to correct refraction. The donor lenticule or lens core may be obtained from other human (allogeneic) or foreign tissue (xenogenic) sources, such as from rabbit, bovine, porcine, or guinea pig corneal tissue. Ocular lenses may also come from transgenic corneal tissue or corneal tissue grown in vitro. In all instances, the architecture of the corneal layers, the normal corneal tissue matrix, e.g., the connective tissue or the stroma, is preserved. The "corneal tissue matrix" is made up of thin layers of collagen fibrils. By the term "donor corneal tissue", as used here, is meant donor or harvested corneas or corneal tissue containing the "corneal tissue matrix". Additionally, it is highly desirable to preserve the anterior surface of the donated corneal tissue as found beneath the native epithelium. The donor corneal tissue is not to undergo treatments such as lyophilization, freezing, or other chemical fixation.

The ocular lens device of this invention desirably includes Bowman's membrane, where the donor tissue includes it, to maintain the native structure of human epithelium. Again, it is highly desirable to harvest from donor sources in such a way that the native anterior surface below the epithelium is preserved. I have found that these native structures have a superior ability, after the revitalization steps discussed below, to support and maintain the replaced epithelium also discussed below. Clarity of the inventive tissue lens core will be at least 85%, preferably between 75%–100%, and most preferably at least 90% of that of human corneal tissue of corresponding thickness.

The overall diameter of the inventive lens is generally less than about 25 mm and more preferably in between 10 and 15 mm. The thickness of the resulting lens is generally less than 300 μm, more preferably between 5–100 μm.

Figure 3A:
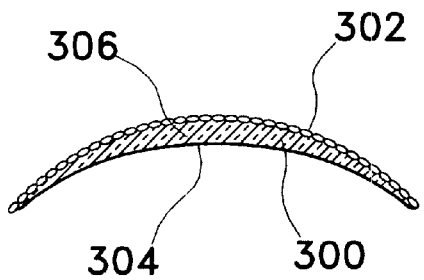
FIG. 3A is a side, cross-sectional view of a pre-fabricated donor lens.
Figure 3B:
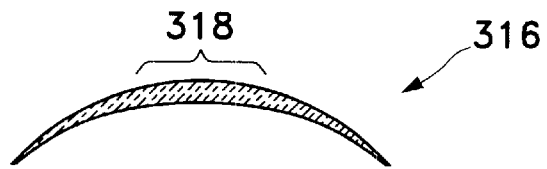
FIG. 3B is a side, cross-sectional view of a pre-fabricated donor lens suitable for correcting myopia.
Figure 3C:
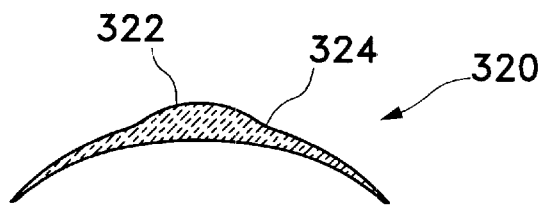
FIG. 3C is a side, cross-sectional view of a pre-fabricated donor lens suitable for correcting aphakia.

As shown in FIG. 3B, a lens core (316) for myopic patients is formed, preferably using the procedures discussed below, in such a way that a generally circular region (318) in the center flattens its anterior curvature. In correction of aphakia, a lens such as is shown in FIG. 3C is formed having a comparatively thicked center (322) and a thinner perimeter (324). In general, the shapes discussed here are similar to those found in the so-called "soft" contact lenses and instruction may be had from that technology relating to the overall form of the lenses selected for correcting specific ocular maladies.

Figure 3D:
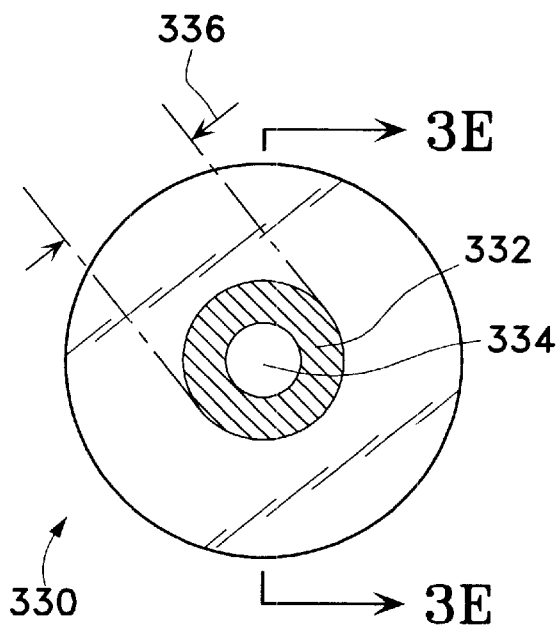
FIG. 3D is a front view of a pre-fabricated donor lens suitable for bifocal use.
Figure 3E:
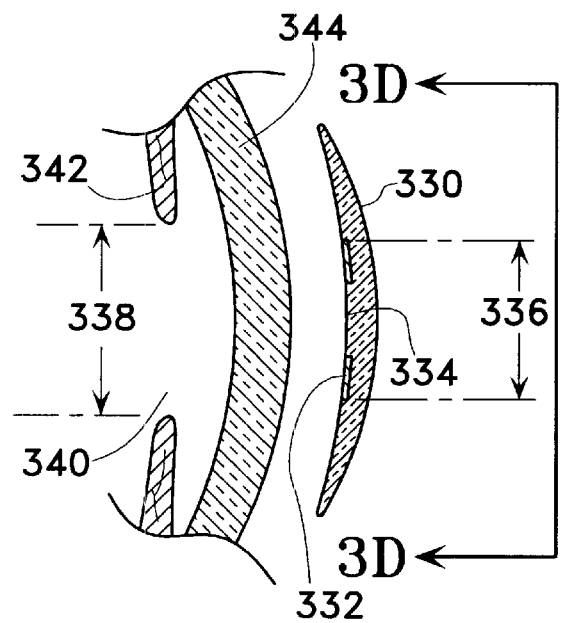
FIG. 3E is a side, cross-sectional view of the FIG. 3C lens positioned away from the cornea of an eye.

As shown in FIGS. 3D and 3E, the inventive lens may also be used to correct presbyopia. In particular, to treat presbyopia, the lens (330) is also provided with an generally opaque annular region (332) in the center. The open center (334) preferably has plano-lens characteristics and an effective diameter of less than about 1.5 mm, preferably between about 0.5–1.5 mm, and most preferably between 0.75 mm and 1.75 mm. The diameter of the central area or "pinhole" is generally formed to be less than the pupillary diameter of the eye in daylight. This creates a "pin-hole" effect, thereby lengthening the overall focal length of the eye and minimizing the need for the eye to accommodate. Other bifocal lens designs can also be incorporated, e.g., concentric, segmented, or progressive diffractive.

FIG. 3E shows a side, cross-sectional view of the inventive lens (330) adjacent the anterior surface of a cornea (344) to illustrate certain features of this variation. The outer diameter (336) of the opaque annular ring (332) is generally selected so that it is smaller than the diameter (338) of the pupil (340) in the iris (342) in low light conditions. In this way, the eye's cornea and lens and the inventive lens cooperate in such a way that incident light passes both though the center of the opaque ring (334), but more importantly, around the periphery of the opaque ring (332), to allow corrected sight during low light conditions.

The annular ring may be situated on the lens core either by placement of a suitable dye, i.e., by "tattooing", or by placement of an opaque biocompatible member of, e.g., Dacron mesh or the like, on the posterior surface to filter light rays.

Shaping Step

Returning to FIG. 3A, the donor ocular lens (300) desirably is obtained after slicing corneal tissue from the donor with a microkeratome to form a lens core. The donor lens has a structural surface, the anterior surface of the lens core being the structural surface of the donor corneal tissue. The lens core anterior surface is harvested preferably to retain the Bowman's membrane (where the donor lens contains one) and epithelium (302). The posterior surface (304) of the resulting inventive lens is generally concave in shape. It is made so by a shaping step which preferably involves the use of an ablative laser, such as an excimer laser, to obtain the necessary power of the lens. Another suitable forming step is high pressure water jet cutting.

Sterilization, Devitalization, and Revitalization Steps

Although the order of the process steps outlined below is typical, it should be understood that such steps may be varied as needed to produce the desired result.

Generally, the lens will first be shaped to an appropriate shape as discussed above. The lens core may then be subjected to processes of sterilization, devitalization, and revitalization. Removal of epithelium (de-epithelialization) and keratocytes (acellularization) from the donor lens will be referred to as "devitalization". The addition of human epithelium and keratocytes will be referred to as "revitalization". One desirable method for accomplishing those steps is found just below. Other methods are known.

Phosphate buffered saline (PBS) with antibiotics, epithelial cell media, and keratocyte media are solutions used during these processes. The "PBS with antibiotics" solution may contain:

PBS with antibiotics
1. Amphotericin B (ICN Biomedicals) 0.625 μg/ml
2. Penicillin (Gibco BRL) 100 IU/ml
3. Streptomycin (Gibco BRL) 100 μg/ml
4. Phosphate buffered saline (Gibco BRL)

The composition of the epithelial cell media may include:

Epithelial cell media
1. Dulbecco's Modified Eagle Media/Ham's F12 media (Gibco BRL) 3:1
2. 10% fetal calf serum (Gibco BRL)
3. Epidermal growth factor (ICN Biomedicals) 10 ng/ml
4. Hydrocortisone (Sigma-Aldrich) 0.4 μg/ml
5. Cholera toxin (ICN Biomedicals) $10^{-10}$ M
6. Adenine (Sigma-Aldrich) $1.8 \times 10^{-4}$ M
7. Insulin (ICN Biomedicals) 5 μg/ml
8. Transferrin (ICN Biomedicals) 5 μg/ml
9. Glutamine (Sigma-Aldrich) $2 \times 10^{-3}$ M
10. Triiodothyronine (ICN Biomedicals) $2 \times 10^{-7}$ M
11. Amphotericin B (ICN Biomedicals) 0.625 μg/ml
12. Penicillin (Gibco BRL) 100 IU/ml
13. Streptomycin (Gibco BRL) 100 μg/ml The composition of the keratocyte media may include:

Keratocyte media
1. DMEM
2. 10% neonatal calf serum (Gibco BRL)
3. Glutamine (Sigma-Aldrich) $2 \times 10^{-3}$ M
4. Amphotericin B (ICN Biomedicals) 0.625 μg/ml Sterilization Step After harvesting the lens core from donor corneal tissue and following the shaping step, the lens may be sterilized by immersion into 98% glycerol at room temperature. Three weeks of glycerol treatment inactivates intracellular viruses and any bacteria or fungi. Ethylene oxide gas sterilization may also be used, but tends to induce variable damage to stromal tissue.

Devitalization Step

De-epithelialization

Following sterilization, I prefer to de-epithelialize the donor lens by placing it in sterile PBS with antibiotics for four hours and changing the solution many times. The lens core may then be kept submerged in the PBS solution at 37° C. for one week to produce a split between the epithelium and the stroma. The epithelium may then be removed, e.g., by physically scraping or washing with a liquid stream. Small numbers of lenses may be stripped of epithelium by gentle scraping with forceps.

Acellularization

The de-epithelialized lens may then be immersed in sterile PBS with antibiotics for an appropriate period, e.g., several weeks, perhaps six weeks to remove native keratocytes. The solution may be changed twice weekly. In some instances, it may not be necessary to remove keratocytes from the donor lens, e.g., when the donor tissue is obtained from a transgenic source and has minimal antigenicity.

Revitalization Step

Preparation of cells

Human epithelial cells and keratocytes are used in the revitalization process. Epithelial cells may be obtained from a tissue bank, but are preferably obtained from fetal or neonatal tissue. Fetal cells are most preferable, since the properties of fetal tissue minimize scarring during the wound healing process.

In any event, freshly isolated epithelial cells, obtained by trypsinization of corneal tissue, may be seeded onto a precoated feeder layer of lethally irradiated 3T3 fibroblasts (i.3T3) in epithelial cell media. Cells are cultured and media changed every three days until the cells are 80% confluent, about 7–9 days. Residual i.3T3 are removed with 0.02% EDTA (Sigma-Aldrich) before the epithelial cells are detached using trypsin (ICN Biomedicals). Another method of regenerating epithelium involves culturing autologous epithelial cells on human amniotic membrane as described in Tsai et al. (2000). "Reconstruction of Damaged Corneas by Transplantation of Autologous Limbal Epithelial Cells," *New England Journal of Medicine* 343:86–93.

Keratocytes may be extracted from the remaining stromal tissue. The stroma is washed in PBS, finely minced, and placed in 0.5% collagenase A (ICN Biomedicals) at 37° C. for 16 hours. Keratocytes obtained from this enzyme digest are then serially cultured in keratocyte media. The epithelial cells and keratocytes generated in the revitalization step will be referred to as "replaced" epithelium and keratocytes.

Production of the Donor Lens

The acellular donor lens core may then be placed on a hydophilic, polyelectrolyte gel for completion of the re-vitalization. The preferred polyelectrolytes are chondroitin sulfate, hyaluronic acid, and polyacrylamide. Most preferred is polyacrylic acid. The lens is immersed in keratocyte media and incubated with approximately $3 \times 10^5$ keratocytes for 48 hours at 37° C. Approximately the same amount of epithelial cells are then added to the anterior stromal surface. Tissue culture incubation continues for another 48 hours. Keratocyte media is changed every two to three days. Once the epithelium is regenerated, the polyelectrolyte gel draws water out of the lens at a pressure of about 20–30 mm Hg until the original lens dimensions are obtained.

Replaced epithelium covers at least a portion of the anterior surface and replaced keratocytes repopulate the stroma of the lens core after revitalization. It may be beneficial in some instances to incorporate therapeutic agents, growth factors, or immunosuppressive agents into the lens core to further decrease the risk of rejection or remedy disease states.

Placement of the Lens on the Eye

Figure 4A:
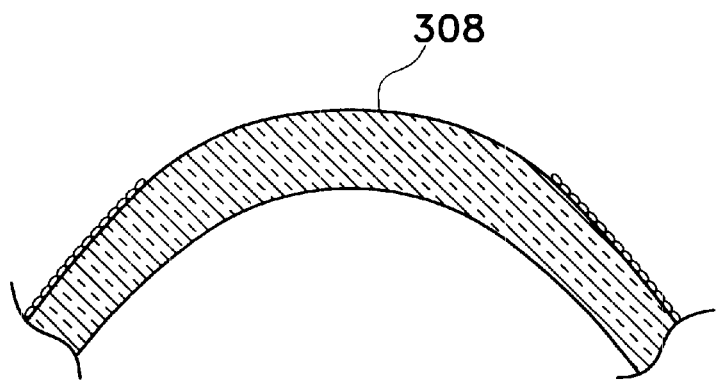
FIG. 4A is a side, cross-sectional view of an area of de-epithelialized recipient cornea prepared to receive the optical lens of the present invention.
Figure 4B:
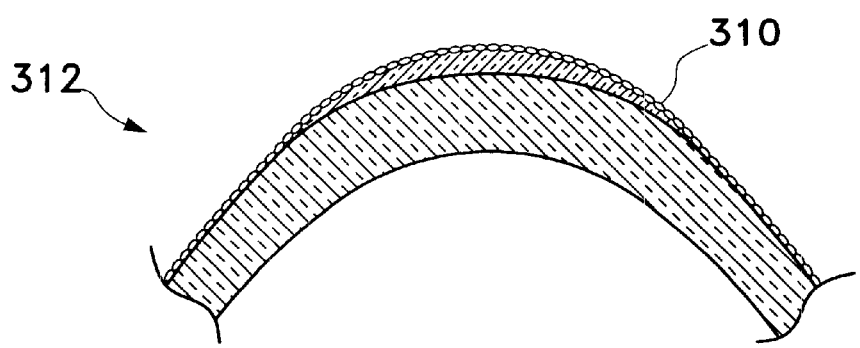
FIG. 4B is a side, cross-sectional view of the donor lens after placement on recipient cornea.

During the procedure, the donor lens (300) is placed on a portion of recipient cornea that has been de-epithelialized (308). The result is the construct (312) shown in FIG. 4B. The lens' replaced epithelium and the host epithelium eventually grow to form a continuous, water-tight layer (310). I have found that the inventive lens bonds to recipient cornea without sutures or adhesives, but can also be removed without substantial difficulty.

I have described the structural and physiologic properties and benefits of this donor ocular lens. This manner of describing the invention should not, however, be taken as limiting the scope of the invention in any way.

I claim as my invention:

1. An ocular lens device comprising:
   a lens core comprising donor corneal tissue having a generally convex anterior surface and a posterior surface, the lens core not having been frozen, lyophilized, or chemically treated by a fixative, and having replaced keratocytes in said lens core or replaced epithelial cells covering at least a portion of said anterior surface.

2. The ocular lens device of claim 1 wherein said posterior surface is generally concave.

3. The ocular lens device of claim 1 wherein said lens core comprises acellular corneal tissue.

4. The ocular lens device of claim 1 wherein said lens core consists essentially of acellular corneal tissue.

5. The ocular lens device of claim 1 wherein said posterior surface is concave.

6. The ocular lens device of claim 1 wherein said posterior surface has been subjected to a shaping step.

7. The ocular lens device of claim 6 wherein said posterior surface is shaped by an ablative laser.

8. The ocular lens device of claim 1 wherein said ocular lens has a clarity at least 85% of that of human corneal tissue of a corresponding thickness.

9. The ocular lens device of claim 1 wherein said ocular lens has a clarity between about 75% and about 100% of that of human corneal tissue of a corresponding thickness.

10. The ocular lens device of claim 9 wherein said lens core has a clarity at least 90% of that of human corneal tissue of a corresponding thickness.

11. The ocular lens device of claim 1 wherein said lens core comprises human corneal tissue.

12. The ocular lens device of claim 1 wherein said lens core comprises allogenic corneal tissue.

13. The ocular lens device of claim 1 wherein said lens core comprises xenogenic corneal tissue.

14. The ocular lens device of claim 13 wherein said xenogenic lens core comprises corneal tissue selected from the group consisting of rabbit, bovine, porcine, and guinea pig corneal tissue.

15. The ocular lens device of claim 1 wherein said lens core comprises transgenic corneal tissue.

16. The ocular lens device of claim 1 wherein said donor corneal tissue has a structural surface and said lens core anterior surface is the structural surface of the donor corneal tissue.

17. The ocular lens device of claim 1 having a size and configuration selected to be corrective for at least one selected from the group consisting of astigmatism, myopia, aphakia, and presbyopia.

18. The ocular lens device of claim 17 wherein said size and configuration is selected to be corrective for myopia and said device has a generally circular, flat lens core center region.

19. The ocular lens device of claim 17 wherein said size and configuration is selected to be corrective for aphakia and said device has a generally flattened perimeter.

20. The ocular lens device of claim 17 wherein said size and configuration is selected to be corrective for presbyopia and has generally circular lens core central region without correction.

21. The ocular lens device of claim 17 wherein said size and configuration is selected to be bifocal.

22. The ocular lens device of claim 20 wherein said lens core further comprises an opaque annular ring having a central open region and peripheral diameter.

23. The ocular lens device of claim 22 wherein said opaque annular ring is formed by tatooing or placement of opaque material on said posterior surface.

24. The ocular lens device of claim 22 wherein said central open region has a diameter less than about 1.5 mm.

25. The ocular lens device of claim 24 wherein said central open region has a diameter between about 0.5 mm and about 1.5 mm.

26. The ocular lens device of claim 24 wherein said central open region has a diameter between about 0.75 mm and about 1.25 mm.

27. The ocular lens device of claim 22 wherein said opaque annular ring comprises a polyethylene terephthalate mesh.

28. The ocular lens device of claim 22 wherein said ring peripheral diameter is between 3–5 mm.

29. The ocular lens device of claim 28 wherein said ring peripheral diameter is selected to be less than the pupillary diameter of a selected recipient eye in low light.

30. The ocular lens device of claim 1 wherein said lens core further contains a therapeutic agent, immunosuppresive agent, or growth factors.

31. The ocular lens device of claim 1 wherein said lens core is comprised of corneal tissue grown in vitro.

32. The ocular lens device of claim 1 wherein said epithelial cells and keratocytes comprise human corneal cells.

33. The ocular lens device of claim 32 wherein said epithelial cells and keratocytes comprise neonatal, fetal, or tissue bank corneal cells.

34. The ocular lens device of claim 1 wherein said lens core has a thickness and said thickness is less than 300 μm.

35. The ocular lens device of claim 34 wherein said lens core thickness is between 5–100 μm.

36. The ocular lens device of claim 1 wherein said lens core has replaced keratocytes.

37. The ocular lens device of claim 1 wherein said lens core has replaced epithelial cells covering at least a portion of said anterior surface.

38. An ocular lens device for introduction into an eye comprising:
a lens core comprising donor corneal tissue having a generally convex anterior surface and a posterior surface, and having replaced keratocytes in said lens core or replaced epithelial cells covering at least a portion of said anterior surface prior to introduction into said eye.

39. The ocular lens device of claim 38 wherein said posterior surface is generally concave.

40. The ocular lens device of claim 38 wherein said lens core comprises acellular corneal tissue.

41. The ocular lens device of claim 38 wherein said lens core consists essentially of acellular corneal tissue.

42. The ocular lens device of claim 38 wherein said posterior surface is concave.

43. The ocular lens device of claim 38 wherein said posterior surface has been subjected to a shaping step.

44. The ocular lens device of claim 43 wherein said posterior surface is shaped by an ablative laser.

45. The ocular lens device of claim 38 wherein said ocular lens has a clarity at least 85% of that of human corneal tissue of a corresponding thickness.

46. The ocular lens device of claim 38 wherein said ocular lens has a clarity between about 75% and about 100% of that of human corneal tissue of a corresponding thickness.

47. The ocular lens device of claim 46 wherein said lens core has a clarity at least 90% of that of human corneal tissue of a corresponding thickness.

48. The ocular lens device of claim 38 wherein said lens core comprises human corneal tissue.

49. The ocular lens device of claim 38 wherein said lens core comprises allogenic corneal tissue.

50. The ocular lens device of claim 38 wherein said lens core comprises xenogenic corneal tissue.

51. The ocular lens device of claim 50 wherein said xenogenic lens core comprises corneal tissue selected from the group consisting of rabbit, bovine, porcine, and guinea pig corneal tissue.

52. The ocular lens device of claim 38 wherein said lens core comprises transgenic corneal tissue.

53. The ocular lens device of claim 38 wherein said donor corneal tissue has a structural surface and said lens core anterior surface is the structural surface of the donor corneal tissue.

54. The ocular lens device of claim 38 having a size and configuration selected to be corrective for at least one selected from the group consisting of astigmatism, myopia, aphakia, and presbyopia.

55. The ocular lens device of claim 54 having a size and configuration selected to be corrective for myopia and said device has a generally circular, flat lens core center region.

56. The ocular lens device of claim 54 wherein said size and configuration is selected to be corrective for aphakia and said device has a generally flattened perimeter.

57. The ocular lens device of claim 54 wherein said size and configuration is selected to be corrective for presbyopia and has a generally circular lens core central region without correction.

58. The ocular lens device of claim 54 wherein said size and configuration is selected to be bifocal.

59. The ocular lens device of claim 57 wherein said lens core further comprises an opaque annular ring having a central open region and peripheral diameter.

60. The ocular lens device of claim 59 wherein said opaque annular ring is formed by tatooing or placement of opaque material on said posterior surface.

61. The ocular lens device of claim 59 wherein said central open region has a diameter less than about 1.5 mm.

62. The ocular lens device of claim 61 wherein said central open region has a diameter between about 0.5 mm and less than about 1.5 mm.

63. The ocular lens device of claim 61 wherein said central open region has a diameter between about 0.75 mm and about 1.25 mm.

64. The ocular lens device of claim 59 wherein said opaque annular ring comprises a polyethylene terephthalate mesh.

65. The ocular lens device of claim 59 wherein said peripheral diameter is between 3–5 mm.

66. The ocular lens device of claim 65 wherein said peripheral diameter is selected to be less than the pupillary diameter of a selected recipient eye in low light.

67. The ocular lens device of claim 38 wherein said lens core further contains a therapeutic agent, immunosuppressive agent, or growth factors.

68. The ocular lens device of claim 38 wherein said lens core has not been frozen, lyophilized, or chemically treated by a fixative.

69. The ocular lens device of claim 38 wherein said lens core is comprised of corneal tissue grown in vitro.

70. The ocular lens device of claim 38 wherein said epithelial cells and keratocytes comprise human corneal cells.

71. The ocular lens device of claim 70 wherein said epithelial cells and keratocytes comprise neonatal, fetal, or tissue bank corneal cells.

72. The ocular lens device of claim 38 wherein said lens core has a thickness and said thickness is less than 300 μm.

73. The ocular lens device of claim 72 wherein said lens core thickness is between 5–100 µm.

74. The ocular lens device of claim 38 wherein said lens core includes replaced keratocytes.

75. The ocular lens device of claim 38 wherein said lens core includes replaced epithelial cells covering at least a portion of said anterior surface.

76. An ocular lens device for correction of presbyopia comprising:

a lens core comprising donor corneal tissue having a generally convex anterior surface and a posterior surface, having replaced keratocytes in said lens core or replaced epithelial cells covering at least a portion of said anterior surface, having a size and configuration selected to be corrective for presbyopia, and a generally circular lens core central region without correction.

77. The ocular lens device of claim 76 wherein said lens core further comprises an opaque annular ring having a central open region and a ring peripheral diameter.

78. The ocular lens device of claim 77 wherein said opaque annular ring is formed by tatooing or placement of opaque material on said posterior surface.

79. The ocular lens device of claim 77 wherein said central open region has a diameter less than about 1.5 mm.

80. The ocular lens device of claim 79 wherein said central open region has a diameter between about 0.5 mm and less than about 1.5 mm.

81. The ocular lens device of claim 79 wherein said central open region has a diameter between about 0.75 mm and about 1.25 mm.

82. The ocular lens device of claim 79 wherein said opaque annular ring comprises a polyethylene terephthalate mesh.

83. The ocular lens device of claim 77 wherein said ring peripheral diameter is between 3–5 mm.

84. The ocular lens device of claim 77 wherein said ring peripheral diameter is selected to be less than the pupillary diameter of a selected recipient eye in low light.

85. A method for correcting the vision of a human eye having a cornea with an anterior surface, comprising the steps of:

a) preparing the anterior of the cornea; and b) introducing the ocular device of any one claims 1–10, 11–30, 31–37, and 38–84 upon said prepared anterior surface.

86. The method of claim 85 wherein said preparing step comprises removing a substantial portion of any epithelial cells present upon the anterior surface.

\* \* \* \* \*

UNITED STATES PATENT AND TRADEMARK OFFICE
CERTIFICATE OF CORRECTION

PATENT NO. : 6,544,286 B1
DATED : April 8, 2003
INVENTOR(S) : Edward Perez

It is certified that error appears in the above-identified patent and that said Letters Patent is hereby corrected as shown below:

<u>Title page,</u>
Item [56], References Cited, U.S. PATENT DOCUMENTS, please add:
-- 6,391,055   5/2002   Ikada --.

Signed and Sealed this

Eighteenth Day of October, 2005

JON W. DUDAS
*Director of the United States Patent and Trademark Office*